US00RE41390E

(19) United States
(12) Reissued Patent
Laurie et al.

(10) Patent Number: US RE41,390 E
(45) **Date of Reissued Patent: *Jun. 22, 2010**

(54) TRACE ELEMENTS

(75) Inventors: Robert Naylor Laurie, Somerset West (ZA); Lamertus Petrus Vosloo, Stellenbosch (ZA)

(73) Assignee: Warburton Technology Limited, Dublin (IR)

( * ) Notice: This patent is subject to a terminal disclaimer.

(21) Appl. No.: 12/353,504

(22) Filed: Jan. 14, 2009

Related U.S. Patent Documents

Reissue of:
(64) Patent No.: 6,638,539
Issued: Oct. 28, 2003
Appl. No.: 09/935,550
Filed: Aug. 24, 2001

(30) Foreign Application Priority Data

Aug. 28, 2000 (ZA) ..... 2000/4456

(51) Int. Cl.
*A61K 33/04* (2006.01)
*A61K 47/00* (2006.01)
*A01N 25/00* (2006.01)
*A01N 59/00* (2006.01)
*A61F 13/00* (2006.01)

(52) U.S. Cl. ..... 424/702; 424/422; 424/439; 424/405; 424/600

(58) Field of Classification Search ..... None
See application file for complete search history.

(56) References Cited

U.S. PATENT DOCUMENTS 4,335,116 A * 6/1982 Howard ..... 514/52

FOREIGN PATENT DOCUMENTS

ZA 826778 * 9/1982

OTHER PUBLICATIONS

Package label from product sold from 1999–2001, identified as Multimin™.

* cited by examiner

*Primary Examiner*—Humera N Sheikh
(74) *Attorney, Agent, or Firm*—Stites & Harbison PLLC; Stephen J. Weyer

(57) ABSTRACT

A method of preparing a trace element solution includes the steps of providing at least one EDTA-complex, providing a sodium selenite solution, and combining the EDTA-complex (es) and the sodium selenite solution to form a trace element solution. A EDTA complex is prepared by using disodium EDTA or EDTA acid, selenium, and any other suitable mineral.

7 Claims, No Drawings

TRACE ELEMENTS

Matter enclosed in heavy brackets [ ] appears in the original patent but forms no part of this reissue specification; matter printed in italics indicates the additions made by reissue.

The invention discloses a method of preparing a trace element solution, which includes the steps of providing at least one EDTA-complex; of providing a sodium selenite solution; and of combining the EDTA-complex(es) and the sodium selenite solution. The invention further discloses at least one EDTA complex prepared by using disodium EDTA or EDTA acid; selenium; and any other suitable mineral.

FIELD OF INVENTION

The present invention relates to trace elements.

BACKGROUND TO INVENTION

It has been found that there is a deficiency of certain trace elements in pastures for livestock in particular areas in South Africa and also in other countries. Various suggestions have been made to provide the required trace elements to such animals. Different chemical compounds and complexes have been investigated for applying the trace elements by way of licks, drenches or injections.

In general the problem with injectable solutions is that there are too low concentrations of the minerals in the solutions. This means that relatively large quantities have to be injected, which in turn cause tissue damage and also abscesses at the site of injection. Furthermore, it is generally the case that different trace elements seldomly are individually sufficient. This means that two or more trace element solutions have to be provided by way of separate injections.

U.S. Pat. No. 4,335,116 (Howard) discloses mineral-containing therapeutic compositions containing EDTA complexes of trace elements. Notably, U.S. Pat. No. 4,335,116 utilises tetra-sodium EDTA, a selenium glycine complex, and metal chlorides for the preparation of the EDTA complexes. Unfortunately, the chloride ions cause contamination and each complex solution is to be made individually. Furthermore, overnight time is required for complexing and heating up afterward to speed up the process requires extra apparatus. If mixtures are required, the individual solutions are to be blocked. If various concentrations as well as compositions are to be made, it can only be done in a cumbersome way, requiring extra apparatus. A further problem may arise when mixtures of high concentration are needed. In certain cases it would be impossible to deliver them, because mixing is always accompanied by dilution.

It is an object of the invention to suggest methods and means for overcoming these problems.

In the specification and claims the expression EDTA refers to ethylene diaminotetraacetic acid ($C_{10},H_{16}O_8N_2$ or $(HO_2CH_2C)_2NCH_2CH_2N\text{-}(CH_2CO_2H)_2$).

SUMMARY OF INVENTION

According to the invention, a method of preparing a trace element solution includes the steps (a) of providing at least one EDTA-complex;

(b) of providing a sodium selenite solution; and (c) of combining the EDTA-complex(es) and the sodium selenite solution.

If more than one EDTA-complex is used, these EDTA-complexes may be prepared in a single continuous process.

The EDTA-complex(es) may be prepared by using disodium EDTA or EDTA acid.

The EDTA-complex(es) may be prepared by using at least one selected from the group consisting of metal oxides, metal hydroxides and metal carbonates.

The EDTA-complex(es) may include at least one of the metal compounds selected from the group consisting of copper, manganese, zinc, molybdenum and chromium.

A trace element solution as prepared by a method as set out herein.

Also, according to the invention, a trace element solution includes (a) at least one EDTA complex prepared by using disodium EDTA or EDTA acid;

(b) selenium; and (c) any other suitable mineral.

The solution may be an injectable solution.

The solution may be a drenchable solution.

Further according to the invention a stock lick includes (a) at least one EDTA complex prepared by using disodium EDTA or EDTA acid;

(b) selenium; and (c) any other suitable mineral.

Also, according to the invention, a method of providing trace elements to animals, such as livestock includes the steps of preparing a trace element solution set out herein and of providing the solution in a suitable quantity to an animal.

DESCRIPTION OF EXAMPLES

The invention will now be described by way of example of injectable solutions in accordance with the invention.

Example 1

Di-Sodium Zinc Ethylene Diamino Tetra Acetate ($C_{10}H_{12}O_8N_2ZnNa_2$) in Water Solution EDTA is suspended in a quantity of distilled water at 50° C. and is stirred continuously. In small proportions firstly sodium hydroxide (NaOH) and then zinc oxide (ZnO) are added in sequence. The pH of the clear solution obtained is measured and brought to 7, if necessary, by either the addition of NaOH (if acid) or EDTA (if alkaline). More distilled water is added to bring the zinc concentration to a predetermined level, and the solution is subsequently filtered.

If 25.16 g zinc oxide, 90.37 g EDTA and 24.74 g NaOH are used and the total volume is 1 liter, the zinc concentration in the solution will be 20 mg/ml.

Example 2

Di-Sodium Manganese Ethylene Diamino Tetra Acetate ($C_{10}H_{12}O_8N_2MnNa_2$) in Water Solution The same method as under example 1 is used with the following variation:

Manganese carbonate ($MnCO_3.xH_2O$) is used in place of zinc oxide.

If 45.45 g manganese carbonate, 106.39 g EDTA and 29.12 g NaOH are used, and the total volume is 1 liter, the manganese concentration will be 20 mg/ml.

Example 3

Di-Sodium Copper Ethylene Diamino Tetra Acetate ($C_{10}H_{12}O_8N_2CuNa_2$) in Water Solution The same method as under Example 1 is followed but with the following variation:

Basic copper carbonate ($CuCO_3Cu(OH)_2.H_2O$) is used in place of the zinc oxide.

If 18.81 g basic copper carbonate, 45.99 g EDTA and 12.59 g NaOH are used, and the total volume is 1 liter, then the copper concentration in the solution will be 10 mg/ml.

Example 4

Mono-Sodium Chromium Diamino Tetra Acetate ($C_{10}H_{12}O_8N_2CrNa$) in Water Solution The same method as under Example 1 is followed, but with the following variation:

Chromium tri-chloride hexahydrate ($CrCl_3.6H_2O$) is used in the place of zinc oxide.

If 25.62 g chromium tri-chloride hexahydrate, 31.59 g EDTA and 15.38 g sodium hydroxide are used and the total is 1 liter, the chromium concentration in the solution will be 5 mg/ml.

Example 5

Sodium Selenite ($Na_2SeO_3.H_2O$) Solution in Water

If 12.09 g sodium selenite is used and the total volume is 1 liter, the selenium concentration in the solution will be 5 mg/ml.

Example 6

A Mixture of the Compounds of Examples 1 to 5

The method is a combination of the above methods under Examples 1, 2, 3, 4 and 5 and takes place as follows:

1. The zinc preparation as per Example 1 is prepared.
2. To this added (in the same container) the chemicals as used for Example 2 for the preparation of the manganese compound.
3. Then the chemicals used as under Example 3 for the preparation of the copper compound are added.
4. At this stage the pH is brought to 7 as described under Example 1 above.
5. Subsequently the chemicals used as under Example 4 for the preparation of the chromium compound are added.
6. Lastly the chemicals used as under Example 5 are added.
7. Finally the total volume is adapted by the addition of distilled water.
8. Filtration takes place.

If 25.16 g zinc oxide, 45.45 g manganese carbonate, 18.81 g basic copper carbonate, 25.62 g chromium tri-chloride hexahydrate, 12.09 g sodium selenite, 274.34 g EDTA and 81.83 g NaOH are used, and if the total volume is 1 liter, then the zinc concentration will be 20 mg/ml, the manganese concentration 20 mg/ml, copper concentration 10 mg/ml, the chromium concentration 5 mg/ml and the selenium concentration 5 mg/ml.

Example 7

Tetra Sodium Molybdenum Tri-Oxide Ethylene Diamino Tetra Acetate ($C_{10}H_{12}O_8N_2MoO_3Na_4$) in Water Solution Molybdenum tri-oxide ($MoO_3$) is suspended at room temperature in a quantity of water and stirred continuously. In portions in sequence firstly sodium hydroxide (NaOH) and then EDTA are added. The pH of the clear solution obtained is measured and it is brought to 7 if required, by adding either NaOH (if acid) or EDTA (if alkaline). More distilled water is added to bring the molybdenum concentration to a pre-determined value. The pH is changed to 6 by the addition of concentrated HCl. Filtration takes place.

If 60.02 g $MoO_3$, 66.71 g NaOH and 121.84 g EDTA are used and if the volume is 1 liter, then the molybdenum concentration will be 40 mg/ml.

In all of the above examples the order of mixing the chemicals may be changed to some extent without any influence on the products formed.

All of the above products can be obtained as solids by evaporation of the appropriate solutions.

All of the above-mentioned chemicals may be substituted by others, provided the substitute are used in equivalent quantities. The particulars are as follows:

1. The di-sodium salt of EDTA in place of EDTA acid.
2. Basic zinc carbonate ($2ZnCO_3.3Zn(OH)_2$) or zinc hydroxide ($Zn(OH)_2$) in place of zinc oxide.
3. Manganese hydroxide ($Mn(OH)_2$) in place of manganese carbonate.
4. Cupric hydroxide ($Cu(OH)_2$) or cupric oxide (CuO) in place of basic copper carbonate.
5. Anhydrous chromium tri-chloride ($CrCl_3$) in place of chromium tri-chloride hexahydrate.
6. Sodium molybdate ($Na_2MoO_4$) in place of molybdenum tri-oxide.

What is claimed is:

1. A method of preparing a trace element solution, said method consisting essentially of the steps of:

(a) preparing a single solution comprising more than one EDTA-complex as a sodium salt in a single continuous process by suspending either disodium EDTA in water or suspending EDTA acid in water with sodium hydroxide, and [adding a] *adding at least one* metal compound selected from the group consisting of metal oxides, metal hydroxides and metal carbonates to the EDTA solution to form the EDTA-complex, *wherein the at least one metal compound comprises at least chromium*; and (b) adding sodium selenite to the solution of EDTA-complexes to form the trace element solution in which the molar ratio of selenium in the form of sodium selenite to the metal compounds to the EDTA complexes varies between 1:4.8:4.8 and 1:19:19.

2. A method as claimed in claim 1, in which the EDTA-complexes comprise at least one of the metal cation components selected from the group consisting of copper, manganese, [zinc,] *zinc and* molybdenum [and chromium].

3. A trace element solution as prepared by a method as claimed in claim 1.

4. A trace element solution as claimed in claim 3, which is an injectable solution.

5. A trace element solution as claimed in claim 3, which is a drenchable solution.

6. A stock lick, which comprises a trace element solution as prepared by a method as claimed in claim 1.

7. A method of providing trace elements to animals, such as livestock, which comprises the steps of preparing a trace element solution as claimed in claim 1, and of providing the solution in a suitable quantity to an animal.

* * * * *